United States Patent
Monteleone et al.

(10) Patent No.: US 7,115,553 B2
(45) Date of Patent: *Oct. 3, 2006

(54) ACETONIDE FRAGRANCE COMPOUND

(75) Inventors: Michael G. Monteleone, Cliffwood Beach, NJ (US); Robert P. Belko, Monroe, NJ (US); Manfred Pawlak, Princeton, NJ (US); Catherine Marie Smith, Parlin, NJ (US); Mark A. Sprecker, Sea Bright, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 183 days.

This patent is subject to a terminal disclaimer.

(21) Appl. No.: 10/618,363

(22) Filed: Jul. 10, 2003

(65) Prior Publication Data

US 2005/0009729 A1    Jan. 13, 2005

(51) Int. Cl.
*C11B 9/00* (2006.01)
(52) U.S. Cl. .............................. 512/12; 512/13; 512/25
(58) Field of Classification Search ................ 512/12, 512/13, 25; 549/359
See application file for complete search history.

(56) References Cited

U.S. PATENT DOCUMENTS

| | | | |
|---|---|---|---|
| 3,422,155 A | 1/1969 | Dowbenko | |
| 3,511,796 A | 5/1970 | Wright | |
| 3,636,165 A | 1/1972 | Hall | |
| 3,647,826 A | 3/1972 | Hall | |
| 3,806,472 A | 4/1974 | Hall | |
| 3,847,993 A | 11/1974 | Hall | |
| 3,927,083 A | 12/1975 | Hall | |
| 4,534,891 A | 8/1985 | Boden et al. | |
| 4,902,840 A | 2/1990 | Sprecker et al. | |
| 5,227,367 A | 7/1993 | Boden et al. | |
| 5,665,698 A | 9/1997 | Narula et al. | |
| 5,733,866 A | 3/1998 | Narula et al. | |
| 6,271,193 B1 | 8/2001 | Beck et al. | |
| 6,303,798 B1 | 10/2001 | Belko et al. | |

FOREIGN PATENT DOCUMENTS

| | | |
|---|---|---|
| DE | 2330648 | 1/1974 |
| EP | 0 395 199 A1 | 10/1990 |
| EP | 0 825 166 A2 | 2/1998 |
| JP | 09249584 | 9/1997 |

*Primary Examiner*—Monique T. Cole

(57) ABSTRACT

A novel compound 4H-indeno[4,5-D]-1,3-dioxole, 3A,5,6,7,8,8B-hexahydro-2,2,6,6,7,8,8-heptamethyl is dislosed as well as the use of the compound as a fragrance chemical. The fragrance compound is suitable for use in creating fragrances, and scents in items such as perfumes, colognes and personal care products.

14 Claims, No Drawings

ACETONIDE FRAGRANCE COMPOUND

FIELD OF THE INVENTION

The present invention is directed to a novel compound and the use of this novel compound as a fragrance chemical suitable for incorporation in fine fragrances, cosmetics, toiletries and related applications.

BACKGROUND OF THE INVENTION

There is an ongoing need in the fragrance industry to provide new chemicals to give perfumers and other persons ability to create new fragrances for perfumes, colognes and personal care products.

U.S. Pat. No. 4,902,840, hereby incorporated by reference, discloses the use of substituted tetrahydroindane derivatives as useful fragrance chemicals. U.S. Pat. No. 6,303,798 hereby incorporated by reference, discloses the use of 4,4a,5,6,7,8,9,9b-octahydro-7,7,8,9,9-pentamethyl-indano[4,5-d]-dioxin as a fragrance chemical.

Despite this disclosure and numerous other patents on fragrance materials, there is a continuing need to provide additional fragrance materials such that perfumers may create new fragrances for various applications.

SUMMARY OF THE INVENTION

The present invention provides a novel chemical, and the use of this chemical to enhance the fragrance of perfumes, toilet waters, colognes, personal products and the like. In addition, the present invention is directed to the use of the novel chemical to enhance fragrance in perfumes, toilet waters, colognes, personal products and the like.

More specifically, the present invention is directed to the novel compound, 4,4a,5,6,7,8,9,9b-octahydro-7,7,8,9,9-pentamethyl-indano[4,5-d]-dioxin, which is understood to be represented by the formula below.

Despite this disclosure and numerous other patents on fragrance materials, there is a continuing need to provide additional fragrance materials such that perfumers may create new fragrances for various applications.

SUMMARY OF THE INVENTION

The present invention is directed to the compound 4H-indeno[4,5-D]-1,3-dioxole, 3A,5,6,7,8,8B-hexahydro-2,2,6,6,7,8,8-heptamethyl use of 4H-indeno[4,5-D]-1,3-dioxole, 3A,5,6,7,8,8B-hexahydro-2,2,6,6,7,8,8-heptamethyl as a fragrance chemical to enhance fragrance in perfumes, toilet waters, colognes, personal products and the like. More specifically, the present invention is direct to the compound having the structure set forth below as well as a method for enhancing a perfume by incorporating an olfactory acceptable amount of compounds of the formula:

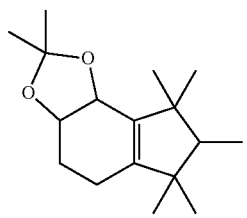

These and other embodiments of the present invention will be apparent by reading the following specification.

DETAILED DESCRIPTION OF THE INVENTION

The compound 4H-indeno[4,5-D]-1,3-dioxole, 3A,5,6,7,8,8B-hexahydro-2,2,6,6,7,8,8-heptamethyl is well suited for incorporation in fragrance formulations. The preparation of the 4H-indeno[4,5-D]-1,3-dioxole, 3A,5,6,7,8,8B-hexahydro-2,2,6,6,7,8,8-heptamethyl is set forth in Example 1 below.

We have discovered that 4H-indeno[4,5-D]-1,3-dioxole, 3A,5,6,7,8,8B-hexahydro-2,2,6,6,7,8,8-heptamethyl has a woody or mossy, odor or note, that is well suited for use as a fragrance chemical.

Those with skill in the art will appreciate that novel compound of the present invention has various isomers. As used throughout this specification 4H-indeno[4,5-D]-1,3-dioxole, 3A,5,6,7,8,8B-hexahydro-2,2,6,6,7,8,8-heptamethyl includes various isomers and isomer blends. The isomers include, but are not limited to the isomers set forth below:

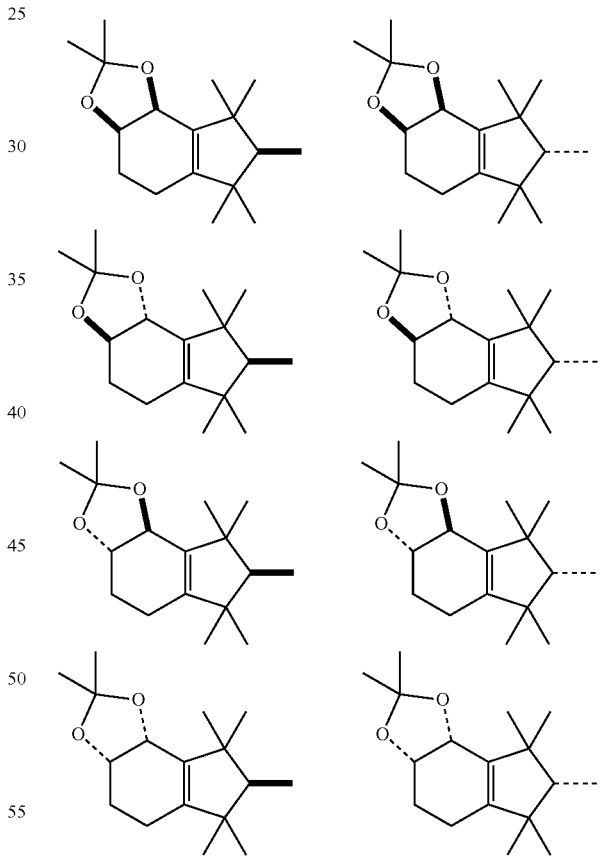

These isomers can be prepared by techniques known in the art. Such techniques include but are not limited to stereoselective dihydroxylation. Other techniques for separating the isomers include distillation and other techniques suitable for separating isomers. The present invention contemplates the use of the stereoisomer mixtures as well as the preparation and/or isolation of the selective isomers.

The use of this novel compound is widely applicable in current perfumery products, including the preparation of perfumes and colognes, the perfuming of personal care products, such as soaps, bath and shower gels, body washes, and hair care products as well as air fresheners, candles and cosmetic products including but not limited to mascara, make-up, eyebrow liner, eyebrow pencil, rouge, cake make-up and the like. The compound can also be used to perfume candles and cleaning agents, such as, but not limited to soaps, detergents, dishwashing materials, scrubbing compositions, window cleaners, and the like.

In these preparations, the compound of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of fragrance ingredient in perfume compositions the individual component will contribute to its particular olfactory characteristics, but the olfactory effect of the perfume composition will be the sum of the effects of each of the perfume or fragrance ingredients. Thus the ingredients of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 20 weight percent, preferably from about 0.01 to about 10 and most preferably from about 0.5 to about 5 weight percent. In addition to the fragrance compound of the present invention, other agents can be used in conjunction with the fragrance. Well known materials such as surfactants, emulsifiers, and polymers to encapsulate the fragrance can also be employed without departing from the scope of the present invention.

Another method of reporting the level of the fragrance compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

The following are provided as specific embodiments of the present invention. Other modifications of this invention will be readily apparent to those skilled in the art, without departing from the scope of this invention. As used herein all percentages are weight percent unless noted to the contrary.

EXAMPLE 1

PREPARATION of
4H-INDENO[4,5-D]-1,3-DIOXOLE,
3A,5,6,7,8,8B-HEXAHYDRO-2,2,6,6,7,8,8-HEPTAMETHYL

A three liter, four neck flask equipped with a stirrer with stir shaft, thermometer, thermowatch, water condenser, addition funnel and isopropyl alcohol/dry ice cooling bath was charged with 15 grams of $BF_3.Et_2O$ and 500 grams of acetone. Five hundred grams of the epoxide, 2H-indeno[4,5]-boxirene, 1A,3,4,5,6,6B-hexahydro-4,4,5,6,6-pentamethylindan, 4,5,epoxy-4,5,6,7-tetrahydro-1,1,2,3,3-pentamethyl (48% by weight) was fed to the reaction flask over a period of two hours. Synthesis of the above epoxy material is described in U.S. Pat. No. 4,902,840, the contents of which are incorporated by reference. The resulting reaction was exothermic and the cooling bath was used to control the reaction temperature to 25–30° C. After the epoxide addition was concluded the reaction was allowed to age for an additional 30 minutes. Water was added to quench the reaction and the layers were separated. The organic phase was washed with saturated Na2CO3 solution. The crude product was recovered [about 513 grams] and was distilled to provide 133 grams of the acetonide, which is about a 43% theoretical yield.

$^1$H NMR (360 MHz, CDCl$_3$) δ4.55 (d, 1H), 4.27 (m, 1H), 2.07 (m, 1H) 1.89 (m, 2H), 1.69 (m, 1H), 1.54 (q, 1H), 1.38 (s, 6H), 1.05 (s, 3H), 1.01 (s, 3H), 0.95 (d, 3H, 0.87 (s, 3H) 0.86 (s, 3H).

EXAMPLE 2

Fragrance Composition Containing the Compound of the Present Invention

DPG is understood to mean dipropylene glycol. Unless noted to the contrary all of the following fragrance materials are available from International Flavors & Fragrances Inc., New York, N.Y.

| Material | Parts |
| --- | --- |
| ARMOISE ESSENCE | 5.0 |
| AMBRETTOLIDE 1% in DPG | 30 |
| Citronellol | 40 |
| Alpha-damascone 10% DEP (Firmenich) | 1 |
| Dimethyl benzyl carbinyl butyrate | 2 |
| DPG | 88 |
| 4-Ethyloctanal | 20 |
| FLOROL (Firmenich) | 6 |
| FRUCTONE | 11 |
| Galbascone 1% (DPG) | 60 |
| Ginger Oil | 1.0 |
| Iso cyclo Citral 1% DPG | 1.0 |
| KOAVONE (IFF) | 36 |
| LIFFAROME "PFG" 10% in DPG | 40 |

-continued

| Material | Parts |
|---|---|
| Litsea cubeba oil | 15 |
| MAGNOLAN (Haarman & Reimer) | 9 |
| Magnolia flower oil 10% in DEP | 4.0 |
| MAGNOLAN | 9.0 |
| Phenyl acetaldehyde (50%) | 2.5 |
| Phenyl ethyl alcohol | 130 |
| Rose oxide 10% in DPG | 13 |
| Triplal Extra | 5.5 |
| VELOUTONE 10% in DPG (Firmenich) | 25 |
| TOTAL | 550.0 |

The compound of the present invention was admixed in DPG to form a 10% solution. Ninety parts of the second solution was admixed with the above fragrance formulation. The resulting formulation was described as having a green, mossy note, partially through the incorporation of 4H-indeno[4,5-D]-1,3-dioxole, 3A,5,6,7,8,8B-hexahydro-2,2,6,6,7,8,8-heptamethyl.

The above fragrance formulation was presented to demonstrate the effectiveness of the compound of the present invention in enhancing, improving or modifying the performance of the formulations in which it is incorporated.

What is claimed is:

1. A method for improving, enhancing or modifying a fragrance through the addition of an olfactory acceptable amount of 4H-indeno[4,5-D]-1,3-dioxole, 3A, 5, 6, 7, 8, 8B-hexahydro-2,2,6,6,7,8,8-heptamethyl.

2. The method of claim 1 wherein the fragrance is incorporated into a product selected from perfumes, colognes, candles, toilet waters, cosmetic products, personal care products, fabric care products, cleaning products and air fresheners.

3. The method of claim 2 wherein the cleaning product is selected from the group consisting of soaps, detergents, dishwashing compositions, scrubbing compounds and window cleaners.

4. The method of claim 2 wherein the product is a personal care product.

5. The method of claim 1 wherein the level is from about 0.005 to about 20 weight percent.

6. The method of claim 1 wherein the level is from about 0.1 to about 10 weight percent.

7. The method of claim 1 wherein the level is from about 0.5 to about 5 weight percent.

8. The compound 4H-indeno[4,5-D]-1,3-dioxole, 3A,5,6,7,8,8B-hexahydro-2,2,6,6,7,8,8-heptamethyl.

9. An olfactory effective amount of the compound of claim 8 which incorporated into a fragrance formulation.

10. The fragrance formulation of claim 9 which is incorporated into a product selected from the group selected from perfumes, colognes, toilet waters, personal care products, cosmetics, cleaning products, candles and air fresheners.

11. The fragrance formulation of claim 10 wherein the cleaning product is selected from detergents, fabric conditioners, dishwashing compositions, scrubbing compounds and window cleaners.

12. The fragrance formulation of claim 10 wherein the personal care product is selected from soaps, bath and shower gels, body washes, and hair care products.

13. A process for preparing the compound 4H-indeno[4,5-D]-1,3-dioxole, 3A,5,6,7,8,8B-hexahydro-2,2,6,6,7,8,8-heptamethyl comprising providing 2H-indeno[4,5]-boxirene, 1A,3,4,5,6,6B-hexahydro-4,4,5,6,6-pentamethylindan and 4,5,epoxy-4,5,6,7-tetrahydro-1,1,2,3,3-pentamethyl;

reacting 2H-indeno[4,5]-boxirene, 1A,3,4,5,6,6B-hexahydro-4,4,5,6,6-pentamethylindan and 4,5,epoxy-4,5,6,7-tetrahydro-1,1,2,3,3-pentamethyl with acetone wherein the reaction temperature is from about 25° C. to about 30° C.

14. The process of claim 13 conducted in the presence of $BF_3 \cdot Et_2O$.

* * * * *